United States Patent [19]

Whitcomb et al.

[11] 4,321,122

[45] Mar. 23, 1982

[54] APPARATUS FOR FORMING ELECTRICAL CONTACT WITH AN ANALYSIS SLIDE

[75] Inventors: Rodney J. Whitcomb, Rochester; Henry S. Adamski, Webster, both of N.Y.

[73] Assignee: Eastman Kodak Company, Rochester, N.Y.

[21] Appl. No.: 135,568

[22] Filed: Mar. 31, 1980

[51] Int. Cl.³ .................... G01N 27/28; G01N 27/46
[52] U.S. Cl. ................... 204/195 R; 324/158 P; 422/63; 422/65
[58] Field of Search .............. 422/63, 64, 65, 66, 422/67; 204/195 R, 1 T; 324/158 P

[56] References Cited

U.S. PATENT DOCUMENTS

| | | | |
|---|---|---|---|
| 3,453,545 | 7/1969 | Oates | 324/158 P |
| 3,549,786 | 12/1970 | Kuo | 174/84 |
| 3,613,001 | 10/1971 | Hostetter | 324/158 P |
| 3,944,922 | 3/1976 | Chambers et al. | 324/158 P |
| 4,027,935 | 6/1977 | Byrnes et al. | 339/48 |
| 4,035,723 | 7/1977 | Kvaternik | 324/158 P |
| 4,053,381 | 10/1977 | Hamblen et al. | 204/195 M |
| 4,123,706 | 10/1978 | Roch | 324/158 P |
| 4,136,007 | 1/1979 | Fujimori | 204/299 R |

OTHER PUBLICATIONS

Research Disclosure, vol. 157, Pub. No. 15767, May 1977.
Research Disclosure, vol. 175, Pub. No. 17569, Nov. 1978.

*Primary Examiner*—G. L. Kaplan
*Attorney, Agent, or Firm*—D. D. Schaper

[57] ABSTRACT

This disclosure relates to a method and apparatus for forming electrical contact with an analysis slide of the potentiometric type. A probe unit, electrically connected to an electrometer, comprises a plurality of probe tips which are adapted to penetrate into the electrodes of an analysis slide and to move laterally in a direction generally parallel to the electrode layers after penetration. A means is provided for preloading the probe tips to control the force required to effect lateral movement of the tips.

20 Claims, 9 Drawing Figures

APPARATUS FOR FORMING ELECTRICAL CONTACT WITH AN ANALYSIS SLIDE

CROSS-REFERENCE TO A RELATED APPLICATION

Reference is made to commonly-assigned U.S. patent application, Ser. No. 054,063, entitled SLIDE TRANSFER MECHANISM, filed in the name of Jessop, on July 2, 1979 and now U.S. Pat. No. 4,269,803.

BACKGROUND OF THE INVENTION

(1) Field of the Invention

This invention relates to apparatus for use in detecting the level of a selected analyte in a biological fluid. More particularly, the invention relates to a method and apparatus for effecting an electrical connection between an electrometer and an analysis slide in a potentiometric analyzer.

(2) State of the Prior Art

Various types of probes are known in the prior art for forming an electrical connection with a relatively thin layer of conductive material deposited on a substrate. For example, in the field of microelectronics, small, accurately-positioned probes have been developed for testing components of a minute size. In the patent to Kvaternik, U.S. Pat. No. 4,035,723, there is disclosed a preloaded probe which is flexed, upon contact of the probe with the surface of a circuit pad, to achieve a bidirectional movement, or scrubbing, of the probe on the surface. The scrubbing action is necessary in the event the surface of the circuit pad is oxidized; however, only a limited amount of scrubbing is desirable, since electrical leads are bonded to the surface after the test.

The patent to Oates, U.S. Pat. No. 3,453,545, discloses apparatus for sequentially testing a plurality of devices on a semiconductor wafer. A mechanism is provided for vibrating the wafer during engagement of a probe mechanism to effect a good connection between the mechanism and the wafer.

The patents discussed above are directed to solutions to the problem of making an electrical connection with a thin conductive layer which is formed on a relatively hard substrate such as a ceramic material. Further, these patents are concerned with forming an electrical connection on the conductive layer, without damaging the layer surface for subsequent electrical use. The Oates patent teaches the undesirability of tearing or gouging through the oxide layer on the contacts because it tends to damage the thin metallic contacts, and further, because it produces nonuniform and nonreproducible test results.

Recent developments have provided analysis slides which can be used to potentiometrically designate the activity of the ions in a liquid test solution. Such slides are formed with a pair of ion-selective electrodes which include thin conductive layers deposited on a relatively soft backing material such as a plastic film. In certain of these slides, a silver chloride layer is formed over the conductive layer; in other configurations, a nickel layer is formed over the conductive layer. A good electrical connection is essential in these slides, since the signal produced in the slide is relatively weak; in some cases, the signal is less than one millivolt. In forming an electrical connection with the analysis slide, a probe must pierce through any layers which overlie the conductive layer. However, the relatively soft backing material creates special problems in forming an electrical connection with the conductive material, since the backing material tends to distort when a probe unit is brought into contact with the layers; thus, the probes do not break through to the conductive layer.

One attempt to overcome the problem of forming an electrical connection with the above-described analysis slide is described in "Research Disclosure," Vol. 175, November 1978, Publication No. 17569, published by Industrial Opportunities Limited, Homewell, Havant Hampshire, PO9 1EF, United Kingdom. The disclosed device comprises a probe biased against the slide by a spring having a relatively-high spring constant. It has been found, however, that simply increasing the spring force on the probe was not totally successful in forming a good electrical connection, since, as noted above, the backing material tended to distort such that the probe was not getting through to the conductive layer.

OBJECTS OF THE INVENTION

It is an object of the invention to overcome the above-described problems of prior-art devices and to provide a novel method and apparatus for effecting an electrical connection between an electrometer and an analysis slide.

Another object of the invention is to provide a method and apparatus for forming an electrical connection with an analysis slide in which a probe unit is adapted to penetrate into the electrodes of a potentiometric analysis slide and to move relative to the slide in a direction generally parallel to the electrodes after penetration to force conductive material into intimate contact with the tips of the probe unit.

Still another object of the invention is to provide a probe unit in which an analysis slide is pivoted in a first direction to move the slide into contact with probe tips and in a second direction to securely hold the analysis slide in a sensing position.

A further object of the invention is to provide a probe unit which can be adjustably preloaded to regulate the depth of penetration into a potentiometric analysis slide.

Other objects and advantages will become apparent from the following Summary and Description of the Preferred Embodiment, when considered in light of the attached drawings.

SUMMARY OF THE INVENTION

This invention relates to apparatus for the clinical analysis of biological fluids in which the fluid is metered onto a generally planar test element, or analysis slide, which is analyzed after an appropriate period of incubation.

More specifically, in accordance with one aspect of the invention, there is provided apparatus for effecting an electrical connection between an electrometer and a generally planar test element in the chemical analysis of a sample fluid, the element comprising a pair of electrodes, each of the electrodes having a plurality of layers including a layer of conductive material formed on a flexible nonconductive support, the apparatus comprising: platform means for receiving a test element and for releasably holding the element during the analysis, the platform means being mounted for movement through a path which extends from a receiving position in which a test element can be loaded onto the platform means to an extended position in which a test element supported on the platform means is electrically connected to the electrometer; a plurality of probe tips electrically connected to the electrometer; means for supporting the tips in the path of the platform means; and actuating means operable on the platform means for moving an element supported on the platform into contact with the tips with a force sufficient to cause the tips to penetrate into the electrodes and for effecting relative movement between the tips and the element in a direction generally parallel to the layers after the penetration, the relative movement causing the tips to plow through the layers to form a ridge of conductive material around the tips.

In a preferred embodiment of the invention, the platform means which supports the test element, or analysis slide, is mounted for pivotal movement to bring the analysis slide into contact with the probe tips. The probe tips are supported on the ends of arms formed of a spring material and mounted in cantilever relation to a clamp in the probe unit support structure; the arms are adapted to flex to permit limited movement of the probe tips. A preload force is applied to the arms which is of a magnitude sufficient to prevent the arms from flexing as the tips penetrate into the element; when the preload force is exceeded, the arms will flex and the tips will move generally parallel to the analysis slide.

The method and apparatus disclosed herein provide a means to effect electrical contact with a thin layer of conductive material in an analysis slide in which the slide is penetrated by the probe tips, and after penetration, the tips are moved generally parallel to the layer to form a ridge of conductive material around the surface of the probe tip. Thus, an effective electrical connection is made by tearing, or plowing, through the conductive layer. An important element in the invention resides in the realization of Applicants that, contrary to prior-art teachings, an effective electrical connection could be made by the described plowing action.

DESCRIPTION OF THE PREFERRED EMBODIMENT

The invention is described hereinafter in connection with an electrometer for use in an analyzer for performing quantitative chemical analyses of biological fluids, such as blood serum. However, the invention is not so limited and it can also be employed in other types of apparatus in which an electrical connection must be made between probe tips and a thin conductive layer formed on a flexible support.

The invention is particularly useful in potentiometric analyzers in which case the substrate which makes the test possible comprises a pair of electrodes selective to the ion activity of choice. Recent developments have provided the electrodes in essentially planar, dry form suitable for use in pairs in an analyzer. An example of such an analyzer is described and claimed in the aforesaid U.S. patent application, Ser. No. 054,063, entitled Slide Transfer Mechanism.

One form of test element which is suitable for use in the apparatus of the subject invention is disclosed in the patent to Hamblen et al., U.S. Pat. No. 4,053,381, granted on Oct. 11, 1977. This patent describes a test element, or analysis slide, of the type which is used to potentiometrically designate the activity of ions in a liquid test solution, and the disclosure of this patent is incorporated herein by reference.

Figure 1:
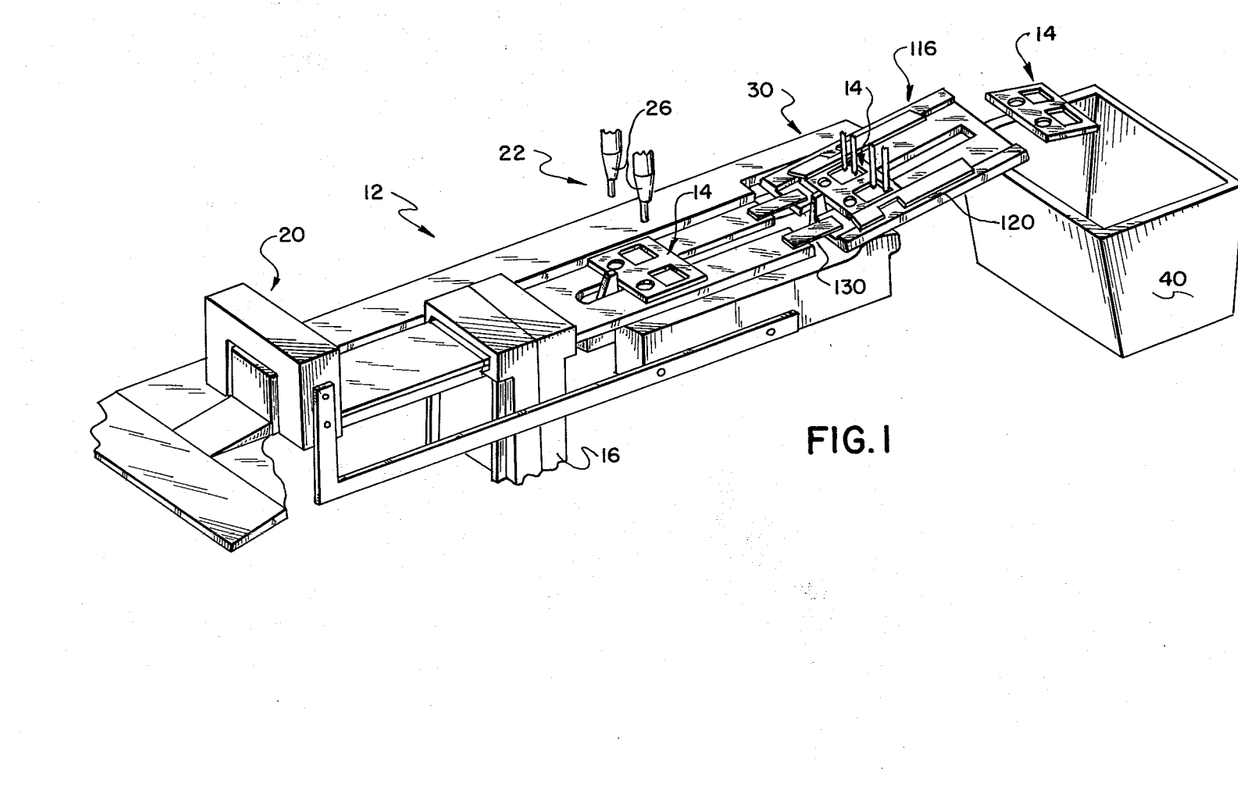
FIG. 1 is a perspective view of a single channel of a potentiometric analyzer of the type which employs the subject invention.

In accordance with a preferred embodiment of the invention, there is shown, in FIG. 1, apparatus 12 which comprises generally the elements embodied in a single channel of a multi-channel potentiometric analyzer for processing an analysis slide 14. Analysis slides 14 are supplied to apparatus 12 in a cartridge 16. A slide transfer mechanism 20 is adapted to remove a slide from cartridge 16 and move it into metering station 22 where a reference fluid and a sample fluid are deposited on the slide through a pair of metering tips 26. After fluids have been deposited on slide 14, the slide is moved from metering station 22 into an analysis station 30 located at the rear of apparatus 12. In analysis station 30, slide 14 is moved into engagement with a plurality of probe tips 33 connected to an electrometer, not shown, which is adapted to measure the potential developed in the analysis slide as a result of the fluids deposited thereon. The method and apparatus for forming an electrical connection between slide 14 and probe tips 33 form the subject of the present invention and will be described in detail hereinafter. After the potential in slide 14 has been measured, the potential being indicative of the activity of a selected ion in the sample fluid, slide 14 is moved into a waste receptacle 40.

Figure 2:
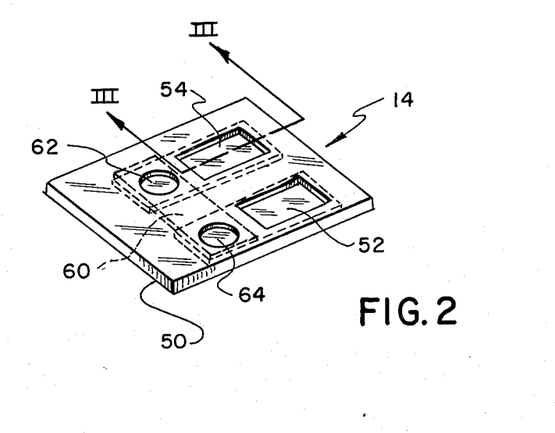
FIG. 2 is a perspective view of an analysis slide of the potentiometric type.
Figure 3:
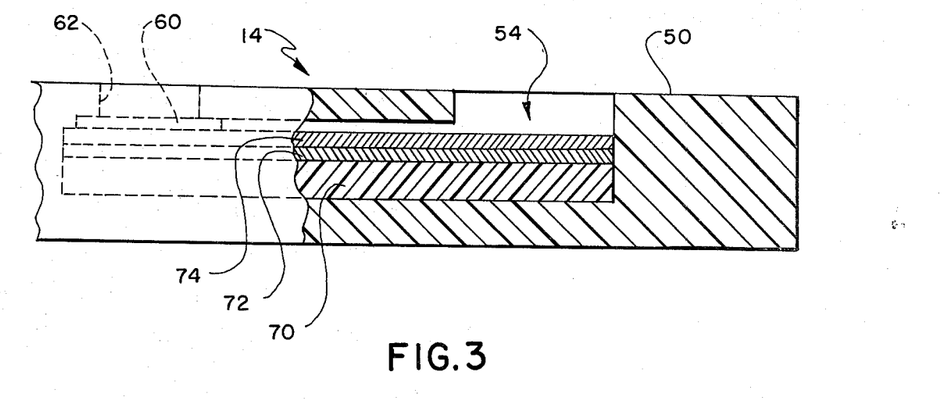
FIG. 3 is a sectional view taken generally along the plane designated as III—III in FIG. 2.

As best shown in FIGS. 2 and 3, analysis slide 14 comprises a frame 50 which is formed of a material that is relatively rigid and is electrically nonconductive. Molded plastics are highly preferred for the material of frame 50, and typical examples of such material include polyethylene or polystyrene. Two solid electrodes 52, 54, are mounted in the frame 50 and are electrically isolated from each other. A bridge, or transport means, 60 is provided for promoting ionic migration between the fluids deposited on the electrodes 52, 54. Apertures 62, 64, are provided in bridge 60 for receiving respectively approximately 10 ul of the sample fluid to be analyzed and approximately 10 ul of reference fluid containing known concentrations of ions under test. An analysis slide, as disclosed herein, is described in more detail in the aforesaid commonly-assigned patent to Hamblen et al., U.S. Pat. No. 4,053,381.

In FIG. 3, there is shown a sectional view through electrode 54 taken along the line III—III in FIG. 2. Electrodes 52 and 54 are identical in analysis slide 14, since a differential mode of measurement is used in which the unknown ion activity of a sample fluid is compared with the known concentration of ions in the reference fluid. Electrode 54 comprises a flexible support 70 which is preferably a plastic or polymeric material, for example, poly (ethylene terepthalate). Coated on support 70 is a layer 72 of conductive material which is preferably silver. Coated over layer 72 is a layer 74 of nickel which will have a thin layer of nickel oxide, not shown, formed thereon as soon as the electrode is exposed to air. In another configuration of slide 14, layer 74 is Ag Cl instead of nickel. The thickness of the layers of electrode 54 has been greatly exaggerated for clarity. In actual practice, the electrodes are generally no greater than 0.20 mm. in thickness. Preferably, analysis slides 14 have sides of 2 to 3 cm. in length and a thickness of 0.13 cm., although it will be apparent that the size of the slide is not critical.

Figure 7:
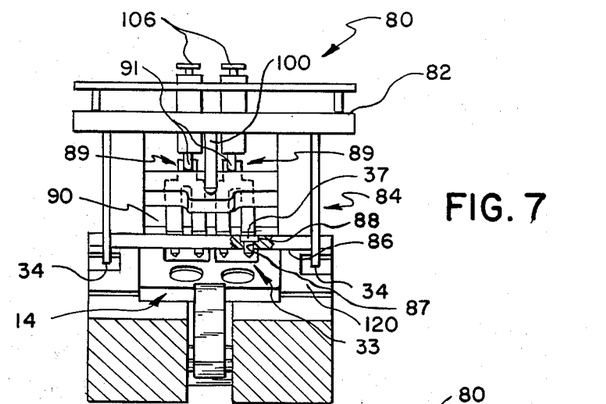
FIG. 7 is a front elevational view of the probe unit, partially in section, and showing the probe tips at the point of initial contact with the analysis slide.
Figure 8:
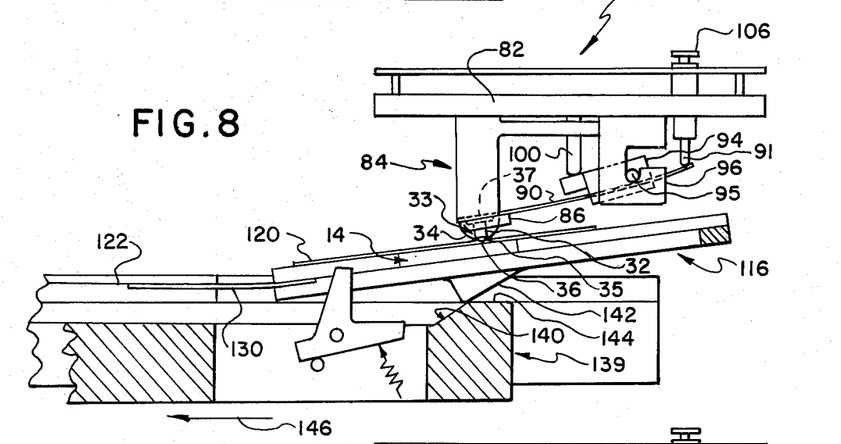
FIG. 8 is a side elevational view of the probe unit and a portion of the slide transfer mechanism, and showing the relative positions of the analysis slide and probe tips when the slide first contacts the tips.
Figure 9:
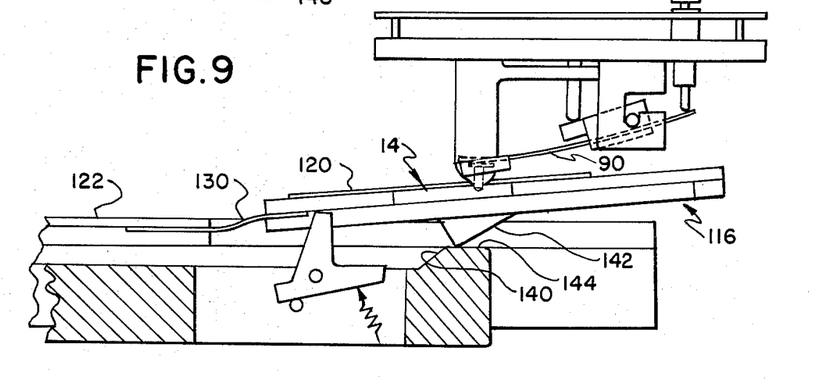
FIG. 9 is a view similar to FIG. 8, but showing the relative positions of the slide and probe tips upon completion of the electrical connection.

A probe unit 80 for forming an electrical connection between an analysis slide 14 and an electrometer, not shown, is shown in FIGS. 7-9. Probe unit 80 comprises a frame 82 and a probe tip support 84 which is connected to frame 82 by means of fasteners not shown. Carried on support 84 is a contact block 86 having four holes 87 therein each of which is adapted to receive a probe tip 33; block 86 is preferably formed of a nonconducting material as, for example, polytetrafluoroethylene, sold under the trademark Teflon. Probe tips 33 have a generally cylindrical body 32, a conical end portion 35 which terminates in a sharp point 36, and an enlarged head 37; head 37 is adapted to seat against a shoulder 88 in a hole 87 in the block 86. (See FIG. 7.) The probe tips 33 are preferably made from a palladium electrical contact alloy, ASTMB 540, which is generally free from corrosion, has high yield strength and hardness, and excellent resistance to abrasion. The cone angle $\beta$ of end portion 35 (FIG. 4) is preferably about 70 degrees and the radius R of point 36 should be less than 0.002 inches.

As shown in FIG. 7, the probe tips 33 are pivotally supported by a pair of bifurcated elements 89. Each of the elements 89 comprises arms 90 and an end portion 91 which is connected to a terminal 106. It will be seen that the two tips 33 on the left, as viewed in FIG. 7, are electrically connected and both are adapted to contact electrode 54 to insure a good connection; similarly the two tips 33 on the right are connected and are adapted to contact electrode 52. Terminals 106 are electrically connected to an electrometer, not shown. Each of the arms 90 is connected to the head 37 of a probe tip 33. (See FIG. 7.) Elements 89 are preferably formed of a spring material such as a berylium-copper alloy. The elements 89 are mounted in a clamp 94 which is pivotally movable on pins 95 supported in a pair of brackets 96 which extend from support 84. Clamp 94 must be electrically isolated from brackets 96 and is preferably formed of a nonconducting material, such as polytetrafluoroethylene, sold under the trademark Teflon. A screw 100 is adapted to be threaded down against clamp 94 to preload probe tips 33. As shown in FIG. 8, when screw 100 is advanced, clamp 94 will move in a counterclockwise direction to increase the tension in arms 90 which are supported in a cantilever relation to clamp 94. The tension in arms 90 is adjusted such that tips 33 will not move from an initial position in block 86 until the tips have penetrated a desired direction into electrodes 52, 54.

Figure 5:
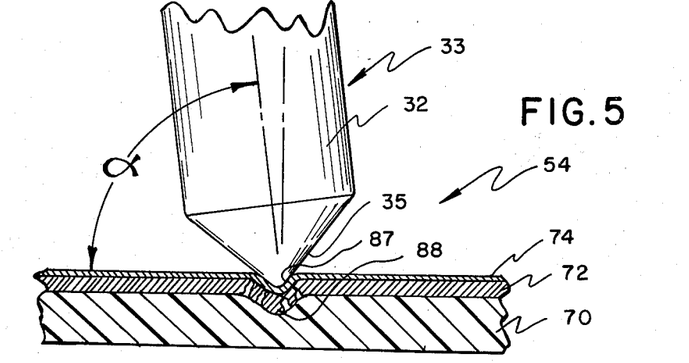
Figure 6:
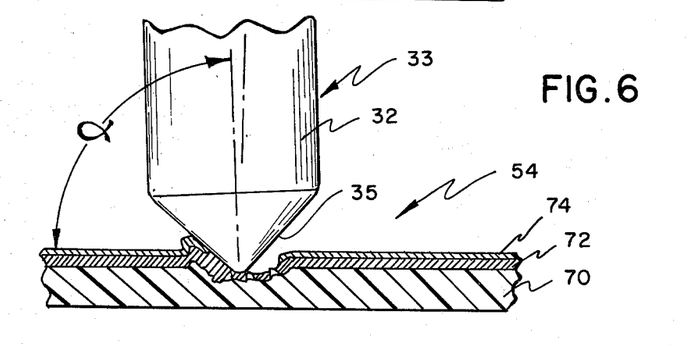

The preload force for each probe tip 33 should be approximately 1.4 oz., the force on tip 33 increasing about 33% at the final, or operative position (shown in FIG. 6). With the described tip geometry and forces, a very high stress will result under points 36, the force exceeding 100,000 PSI if the tips penetrate into electrodes 52, 54, but do not break through layers 74, 72, as shown in FIG. 5. This results in a force high enough to exceed the elastic limit of organic materials and of the thin layers 74, 72, respectively of nickel and silver; as a result, the point 36 fractures the layers 74, 72, as indicated by fracture lines 87, 88, in FIG. 5. In some applications, tips 33 may break through layers 72, 74, and into support 70 before the preload force is overcome; if this occurs, the depth of penetration is limited by the reduction in penetrating stress as the force is distributed over the increasing area of the conical surface of end portion 35. Two important features of the disclosed probe unit 80 include the capability of tip 33 to penetrate any dust or debris encountered on the electrodes 52, 54, of slide 14 and the self-cleaning nature of the tip 33. In use of the tip 33, some of the material from electrodes 52, 54, is collected on tip 33 and is pushed up the conical end portion 35 with successive tests. The lateral motion of tip 33 aids in the cleaning action, and the material periodically falls off, due to its own weight, and is carried away on a slide 14.

A movable platform 116 is adapted to receive an analysis slide 14 and support the slide during the measurement of the potential developed in the slide. Platform 116 includes a pair of spring clips 120 on opposite sides thereof for releasably holding the analysis slide 14 in position during the test procedure. As shown in FIG. 8, platform 116 is mounted for pivotal movement by means of flexible elements 130 which are connected to slide track 122. The platform 116 is movable between a generally horizontal receiving position, not shown, and an extended position, shown in FIG. 9.

An actuating means 139 is operable on platform 116 to raise the platform and a slide 14 supported thereon into contact with probe tips 33. Actuating means 139 comprises a cam 140 on slide transfer mechanism 20 and a projection 142 located along a central portion of platform 116. Slide transfer mechanism 20 is adapted to move rearwardly to deliver a slide 14 into analysis station 30. After delivery of a slide 14 into the analysis station 30, forward movement of transfer mechanism 20, as indicated by arrow 146 in FIG. 8, serves to bring cam 140 into engagement with projection 142 which raises platform 116 into contact with probe tips 33. Continued forward movement of slide transfer mechanism 20 will move slide 14 against tips 33 with sufficient force to overcome the preload force and to cause the tips to penetrate into slide 14; the position of the tips 33 relative to an electrode 54 at the point when the preload force has just been overcome is shown in FIG. 5.

After the preload force has been overcome, additional movement of slide transfer mechanism 20, in the direction of arrow 146, will pivot platform 116 into contact with stops 34 on support 84; this pivotal movement of platform 116, between the point where the preload force is overcome and the point where contact is made with stops 34, causes tips 33 to be lifted off of block 86. As the probe tips are raised off block 86, they will pivot due to the flexure of arms 90, and will plow through the electrode layers 74, 72, as shown in FIG. 6. The plowing, or lateral movement of tips 33 relative to the electrode 52, 54, along a line generally parallel to layers 72, 74, results mainly from the pivotal action of tips 33, rather than from the pivotal movement of platform 116. It will be seen that the desired amount of lateral movement can be controlled by the spacing of the tips relative to the stops in a direction generally perpendicular to platform 116. As projection 142 moves from the position shown in FIG. 8 to the generally horizontal surface 144 of cam 140, the platform 116 will be pivoted slightly about stops 34 in a direction opposite to the previous pivotal movement, and flexible elements 130 will assume a generally S shape. (See FIG. 9).

Figure 4:
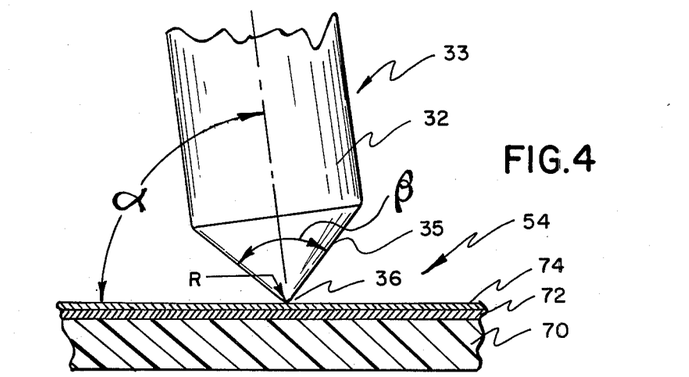
FIGS. 4-6 show the movement of a probe tip relative to an analysis slide from the initial contact of the tip with the slide to the completion of the electrical connection.

As shown in FIGS. 4-6, tips 33 form an angle α with the analysis slide 14 during the test procedure. When tips 33 first contact slide 14, angle α is approximately 80°, and the angle α increases as the tips form an electrical connection with slide 14. It is essential that angle α not become greater than 90° during the test procedure to insure that the tips 33 plow through layers 74, 72, in the proper manner.

It is very important, in achieving an accurate measurement, that the tips 33 be accurately located relative to electrodes 52, 54, and that the tips be firmly held during the measurement of the potential developed in analysis slide 14. The locating and holding functions are accomplished by a three-point support provided by the projection 142 and the stops 34; projection 142, which receives the lifting force from cam 140, is located between stops 34 along a central portion of platform 116. The final movement of platform 116, in which the platform 116 is pivoted about stops 34 serves to lock the platform in its extended position during the measurement on analysis slide 14. To further minimize any movement of the tips 33 relative to electrodes 52, 54, after the platform 116 has contacted stops 34, the stops 34 are positioned in line with tips 33, as shown in FIG. 8.

The disclosed invention provides an extremely effective means of forming an electrical connection between a set of probe tips and a thin conductive layer formed on a relatively flexible substrate such as support 70. In the described device, the probe tips 33 are adapted to move generally perpendicular to electrodes 52, 54, until a preload force on tips 33 is exceeded whereupon the tips move generally parallel to the electrodes 52, 54; in the parallel movement, the tips are adapted to plow through the electrodes, pushing conductive material around the electrode to form a good electrical contact. Although slide 14 is moved into engagement with tips 33 in the above description, it will be apparent that the invention could be practiced by supporting the slide 14 in a horizontal position and mounting the probes for vertical and lateral movement relative to the slide.

The invention has been described in detail with particular reference to preferred embodiments thereof, but it will be understood that variations and modifications can be effected within the spirit and scope of the invention.

What is claimed is:

1. Apparatus for effecting an electrical connection between an electrometer and a generally planar test element in the chemical analysis of a sample fluid, said element comprising a pair of electrodes, each of said electrodes having a plurality of layers including a layer of conductive material formed on a flexible nonconductive support, said apparatus comprising:

platform means for receiving a test element and for releasably holding said element during said analysis, said platform means being mounted for movement through a path which extends from a receiving position in which a test element can be loaded onto the platform means to an extended position in which a test element supported on the platform means is electrically connected to said electrometer;

a plurality of probe tips electrically connected to said electrometer;

means for supporting said tips in the path of said platform means; and actuating means operable on said platform means for moving an element supported on said platform into contact with said tips with a force sufficient to cause said tips to penetrate into said electrodes and for effecting relative movement between said tips and said element in a direction generally parallel to said layers after said penetration, said relative movement causing said tips to plow through said layers to form a ridge of conductive material around said tips.

2. Apparatus, as defined in claim 1, wherein said apparatus comprises stop means, said platform means is pivotally mounted for movement between said receiving position and said extended position, and said platform means is in contact with said stop means in the extended position.

3. Apparatus, as defined in claim 1, wherein said probe tips are pivotally movable between an initial position and an operative position, and said supporting means includes means for applying a preload force which biases said tips into said initial position.

4. Apparatus, as defined in claim 3, wherein said relative movement occurs after said tips have moved away from said initial position.

5. Apparatus, as defined in claim 3, wherein said means for applying a preload force on said tips includes arms fixed to each of said tips and means for tensioning said arms.

6. Apparatus, as defined in claim 3, wherein said tips in said initial position form an angle of about 80 degrees with a test element in contact therewith, and said tips in said operative position form an angle of less than 90 degrees with a test element supported on said platform means in the extended position.

7. Apparatus, as defined in claim 1, wherein said probe tips are generally cylindrical elements having sharp points for contacting said electrodes, and said supporting means comprises a contact block adapted to receive said tips for slidable movement therein.

8. Apparatus, as defined in claim 7, wherein said tips are formed of a palladium alloy.

9. Apparatus, as defined in claim 1, wherein said layer of conductive material is silver and said force is of sufficient magnitude to create a pressure on said tips in excess of the elastic limit of said silver layer.

10. Apparatus, as defined in claim 1, wherein said platform means comprises a projection along a central portion thereof, and said actuating means comprises a slidable member having a cam which cooperates with said projection to move said platform means.

11. Apparatus, as defined in claim 1, wherein said platform means is adapted to pivot in a first direction during a portion of the movement from said receiving position to said extended position and in a second direction during the remainder of said movement.

12. Apparatus for effecting an electrical connection between an electrometer and a generally planar test element adapted for use in the chemical analysis of a sample fluid, said element comprising a pair of electrodes, each of said electrodes having a layer of conductive material formed on a flexible support, said apparatus comprising:

platform means for receiving a test element and for releasably holding the element during said analysis, said platform means being mounted for pivotal movement through a path which extends from a receiving position in which a test element can be loaded onto said platform means to an extended position in which a test element supported on the platform means is electrically connected to said electrometer;

a plurality of probe tips electrically connected to said electrometer;

means for supporting said tips for pivotal movement in the path of said platform means, said tips being movable between an initial position and an operative position, said supporting means including means for applying a preload force which biases said tips into said initial position, said force being of a magnitude sufficient to cause said tips to penetrate into said electrode;

stop means located adjacent said supporting means and in the path of said platform means; and actuating means for pivoting said platform means (1) a first distance from said receiving position to move an element supported on the platform means into contact with said tips (2) an additional distance to move said tips into said electrode, and (3) a further distance to move said platform into contact with said stop means and to effect the movement of said tips relative to said layers along a line generally parallel to the layers.

13. Apparatus for effecting an electrical connection between an electrometer and a generally planar test element in the chemical analysis of a sample fluid, said element comprising a pair of electrodes, each of said electrodes having a plurality of layers including a layer of conductive material formed on a flexible nonconductive support, said apparatus comprising:

platform means for receiving a test element and for releasably holding the element during said analysis;

probe means supported adjacent said platform means and adapted to be electrically connected to said electrometer;

actuating means for moving said platform means and said probe means relative to each other to bring said probe means into contact with the electrodes of a test element received by the platform means with a force sufficient to cause said probe means to penetrate into said electrodes and to effect relative movement between said probe means and said electrodes in a direction generally parallel to said layers after said penetration, said relative movement causing said probe means to plow through said layers to form a ridge of conductive material around said probe means.

14. Apparatus, as defined in claim 13, wherein said probe means comprises a plurality of probe tips.

15. Apparatus, as defined in claim 14, wherein the probe tips are each supported for pivotal movement between an initial position and an operative position.

16. Apparatus, as defined in claim 15, wherein said relative movement occurs after said tips have moved away from said initial position.

17. Apparatus, as defined in claim 16, wherein said probe means comprises means for applying a preload force which biases said tips into said initial position.

18. Apparatus, as defined in claim 17, comprising arms fixed to each of said tips, and wherein the means for applying said preload force includes means for tensioning said arms.

19. Apparatus, as defined in claim 18, comprising supporting means for supporting said probe tips, and wherein said probe tips are generally cylindrical elements having sharp points for contacting said electrodes, and said supporting means comprises a contact block adapted to receive said tips for slidable movement therein.

20. Apparatus, as recited in claim 19, wherein each of said probe tips includes a cone-shaped end portion which includes the point, said end portion forming an angle of about 70 degrees in cross section, and said point having a radius of about 0.002 inches.

* * * * *

UNITED STATES PATENT OFFICE
CERTIFICATE OF CORRECTION

PATENT NO. : 4,321,122
DATED : March 23, 1982
INVENTOR(S) : Rodney J. Whitcomb and Henry S. Adamski It is certified that error appears in the above-identified patent and that said Letters Patent are hereby corrected as shown below:

| | |
|---|---|
| Col. 1, Line 10 | after 1979, insert --,-- |
| Col. 3, Line 35 | delete "of" and substitute therefor --by-- |
| Col. 4, Line 60 | before patent, insert --U.S.-- |
| Col. 5, Line 19 | after fasteners, insert --,-- |
| Col. 5, Line 62 | delete "direction" and substitute therefor --distance-- |
| Col. 6, Line 63 | delete "electrode" and substitute therefor --electrodes-- |

Signed and Sealed this

Twenty-second Day of June 1982

[SEAL]

Attest:

*Attesting Officer*

GERALD J. MOSSINGHOFF
*Commissioner of Patents and Trademarks*